(12) United States Patent
Keller

(10) Patent No.: US 8,016,808 B2
(45) Date of Patent: Sep. 13, 2011

(54) DEVICE FOR PIERCING FILM BAGS

(75) Inventor: Wilhelm A. Keller, Merlischachen (CH)

(73) Assignee: Medmix Systems AG, Rotkreuz (CH)

( * ) Notice: Subject to any disclaimer, the term of this patent is extended or adjusted under 35 U.S.C. 154(b) by 408 days.

(21) Appl. No.: 12/223,328

(22) PCT Filed: Feb. 13, 2007

(86) PCT No.: PCT/CH2007/000070
§ 371 (c)(1),
(2), (4) Date: Jul. 29, 2008

(87) PCT Pub. No.: WO2007/095768
PCT Pub. Date: Aug. 30, 2007

(65) Prior Publication Data
US 2009/0024104 A1    Jan. 22, 2009

(30) Foreign Application Priority Data

Feb. 21, 2006 (CH) .......................... 266/06

(51) Int. Cl.
*A61M 5/32* (2006.01)
*A61B 19/00* (2006.01)
(52) U.S. Cl. ..................... 604/411; 604/408; 604/414

(58) Field of Classification Search ........... 604/403–416
See application file for complete search history.

(56) References Cited

U.S. PATENT DOCUMENTS

| | | | | |
|---|---|---|---|---|
| 4,303,069 | A | * | 12/1981 | Cohen .......................... 604/201 |
| 6,364,163 | B1 | | 4/2002 | Mueller et al. |
| 2002/0113089 | A1 | | 8/2002 | Nehren et al. |

FOREIGN PATENT DOCUMENTS

| | | | |
|---|---|---|---|
| EP | 0 377 287 A | | 7/1990 |
| EP | 0 863 088 B1 | | 9/1998 |
| FR | 2 604 363 | | 4/1988 |
| WO | WO 88/02265 | * | 4/1988 |
| WO | WO-2005/016170 A2 | | 2/2005 |

* cited by examiner

*Primary Examiner* — Leslie R Deak
*Assistant Examiner* — Philip R Wiest
(74) *Attorney, Agent, or Firm* — Foley & Lardner LLP

(57) ABSTRACT

The device for piercing film bags includes a piercing spike and means for preventing unintentional piercing by the piercing spike, the means for preventing unintentional piercing comprising a bag support plate that is connected to a baseplate by collapsible or tearable spacers. The device is preferably designed as a unit and insertable into a container of a dispensing assembly. This device provides a high safety against unintentional piercing due to shocks and transport vibrations and is inexpensive to manufacture and multifunctional.

17 Claims, 4 Drawing Sheets

FIG. 5
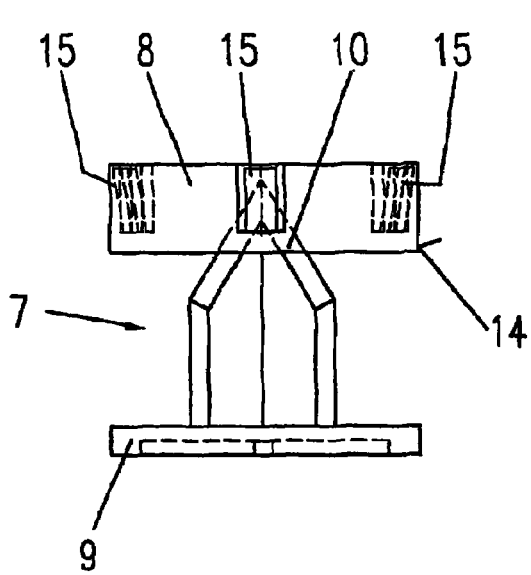
FIG. 6
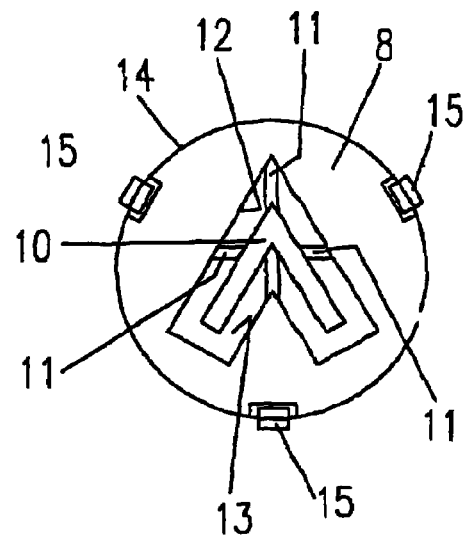
FIG. 7A  FIG. 7B  FIG. 7C  FIG. 7D
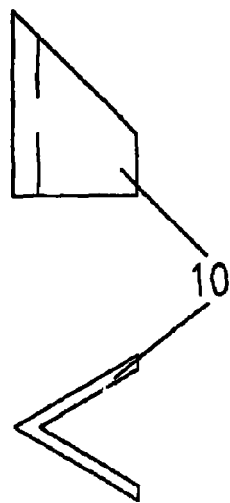 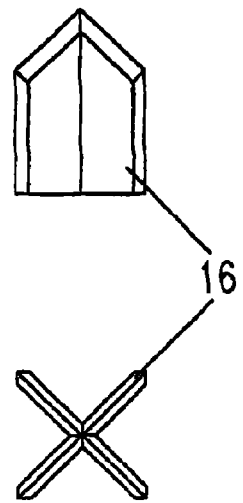  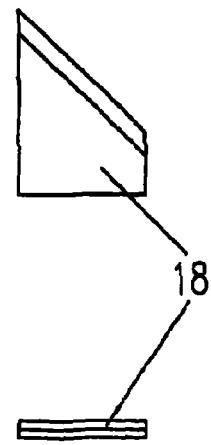

FIG. 8
FIG. 9
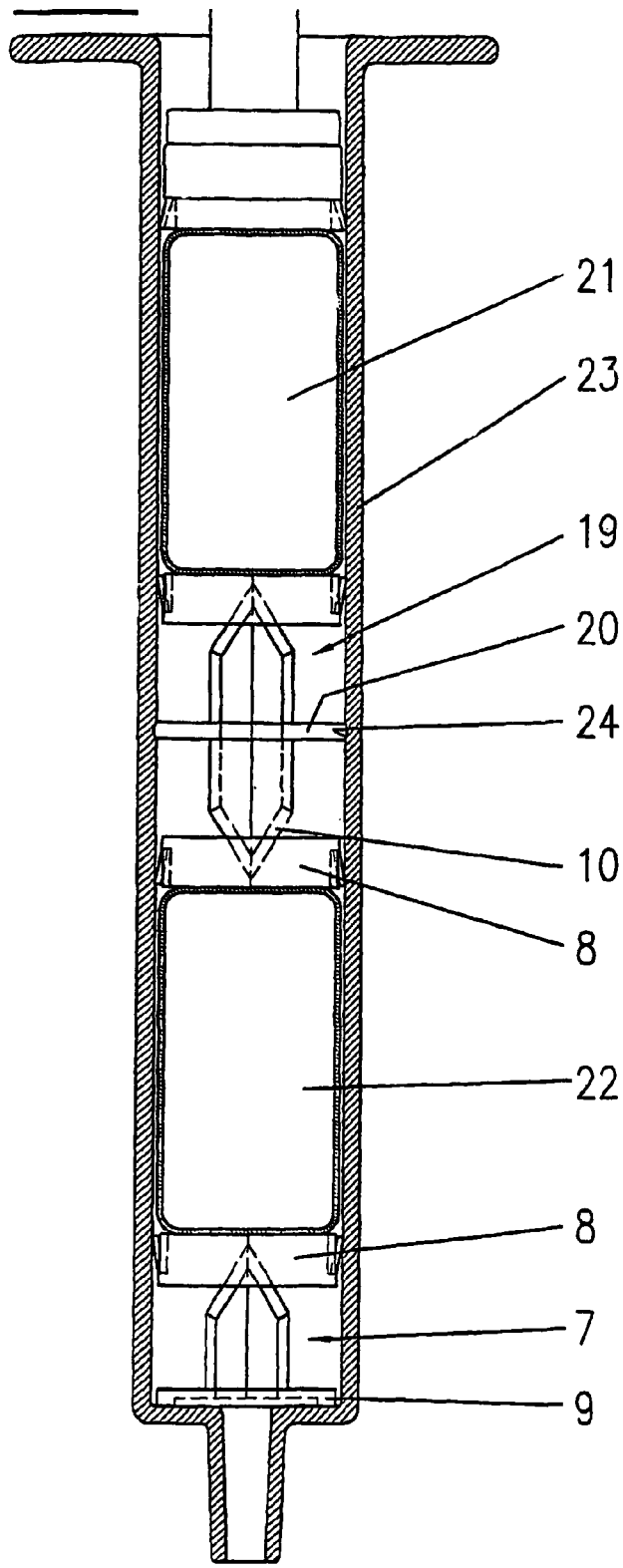
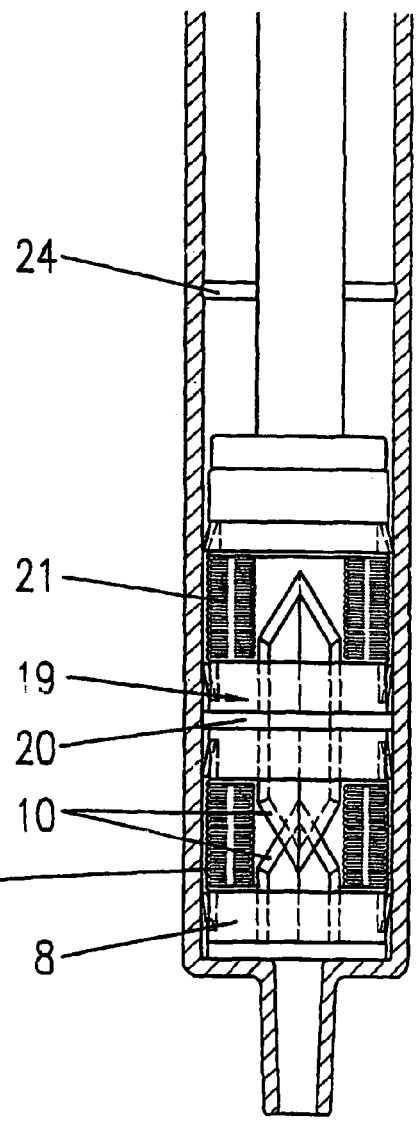

DEVICE FOR PIERCING FILM BAGS

This application is the National Phase of PCT/CH2007/000070, filed Feb. 13, 2007, which claims priority to Switzerland Application No. 00266/06, filed Feb. 21, 2006, the disclosures of which are hereby incorporated by reference in their entirety.

FIELD OF INVENTION

The present invention relates to a device for piercing film bags, including a piercing spike and means for preventing unintentional piercing by the piercing spike.

As is generally known, the manufacturers of medicinal and pharmaceutical products aim to achieve maximum storage stability of their products. The storage life is essentially influenced by the packaging, but packages of synthetic materials have the disadvantage of being gas-permeable. Glass packages are more expensive, their possibilities of design are limited, and glass is furthermore fragile. Combined packages, e.g. glass containers as storage and transport packages and a subsequent transfer of the content to application packages, for example glass vials for storage and plastic syringes for the application, are expensive and laborious to handle.

Especially in the case of syringes, it is desirable to store and transport the substances directly in the application syringe. Therefore, plastic syringes containing products of critical stability are additionally packed in an air- and moisture-tight outer aluminum film bag.

However, the above-mentioned packaging concepts function only conditionally or not at all when two substances of different kinds are stored in one unit, e.g. a single or double syringe, or when a substance is incompatible with the package.

Therefore, a solution is needed that allows liquids, pastes, or powders to be packaged in a bag, e.g. an aluminum film bag, and stored directly in the dispensing assembly, e.g. a syringe. In use, the tube or container should be opened when the dispensing assembly is actuated.

In this regard, one problem is that a device for piercing or opening a tube or container must not be actuatable during transport or handling, on one hand, and on the other hand, that the piercing device should function reliably when operated.

PRIOR ART

A device according to the preamble of claim 1 is disclosed in EP-B1-1 065 153 where the foil package has a cover portion with a receiving headpiece comprising a piercing pin that is located at a distance from the film tube bag in a first position of the cover portion and penetrates the bag in a second position. In this case, the securing means include a locking pin that prevents an unintended movement of the cover portion with the piercing pin toward the bag. The securing mechanism requires various additional parts while the piercing pin is attached to the cover portion.

U.S. Pat. No. 4,303,069 discloses a hypodermic syringe with needle guide, wherein the tubular member of the syringe has a rupturable closure, held by a hub member having a collapsible or corrugated portion. The hollow needle is fixedly attached to a tubular section of the syringe. For use, the collapsible portion is reduced in length and the sharpened end of the needle is freed for being able to pierce the container.

U.S. Pat. No. B1 6,352,177 discloses another dispensing assembly for tube bags where the cover portion has piercing tubes fastened therein and grooves in the outlet respectively bulges on the cover portion prevent that the piercing tubes are unintentionally driven into the bags. This arrangement requires a specific design of the outlet both of the cartridge and of the cover with the piercing tubes integrated in the cover.

In a first embodiment of U.S. Pat. No. 6,012,610, the cartridge inlet is provided with piercing spikes whose height is not the same as that of the surrounding walls of the outlet portion such that only under a certain pressure a part of the film tube reaches the piercing means and is pierced. In further embodiment variants, the piercing spikes have rated breaking locations so that the content of the tube can be emptied as completely as possible without the piercing spikes limiting the stroke of the discharge pistons.

EP-B1-0 863 088 discloses a receiver part for a hose bag that has a piercing mandrel arranged in a recess.

SUMMARY OF THE INVENTION

On the background of this prior art, it is an object of the present invention to provide a device for piercing film bags by actionating the dispensing means, the device, while effectively preventing an unintentional piercing of the bag or container, being simple in its construction and inexpensive to manufacture. This object is attained by a device wherein the means for preventing unintentional piercing comprise a baseplate having a piercing spike on at least one of its side, over which a bag support plate is arranged such that its surface facing the film bag is located above the point of the piercing spike, the bag support plate being connected to the baseplate and/or the piercing spike by spacers being capable to be deformed, or collapsed or torn off.

Another object of the invention is to design the device in such a manner that it can be used with a large number of containers of cartridges and dispensing assemblies without requiring modifications of these containers. This object is attained by a device wherein which is designed as a unit that is insertable into a container of a dispensing assembly.

BRIEF DESCRIPTION OF THE DRAWINGS

The invention will be explained in more detail hereinafter with reference to drawings of exemplary embodiments.

FIG. 5 shows a lateral view of the device of FIG. 4, FIG. 6 shows a top view of the device of FIG. 5, FIGS. 7A-7D show four variants of the piercing spike of the device of the invention, FIG. 8 shows an embodiment with a container containing two film bags in the operational condition, and FIG. 9 shows the arrangement of FIG. 8 in the emptied condition.

DETAILED DESCRIPTION OF PREFERRED EMBODIMENTS

Figure 1:
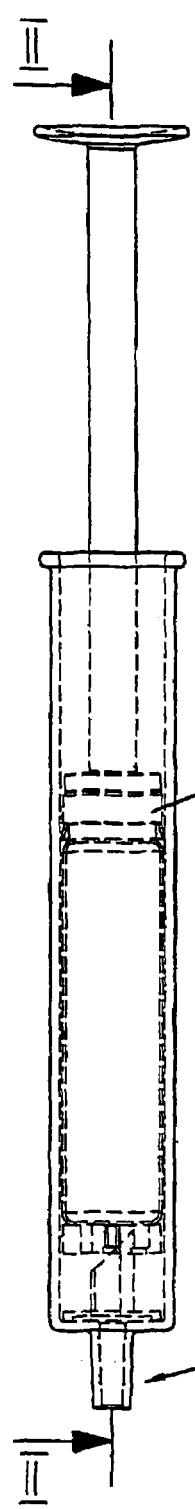
FIG. 1 shows a lateral view of a device according to the invention within a container of a cartridge.
Figure 2:
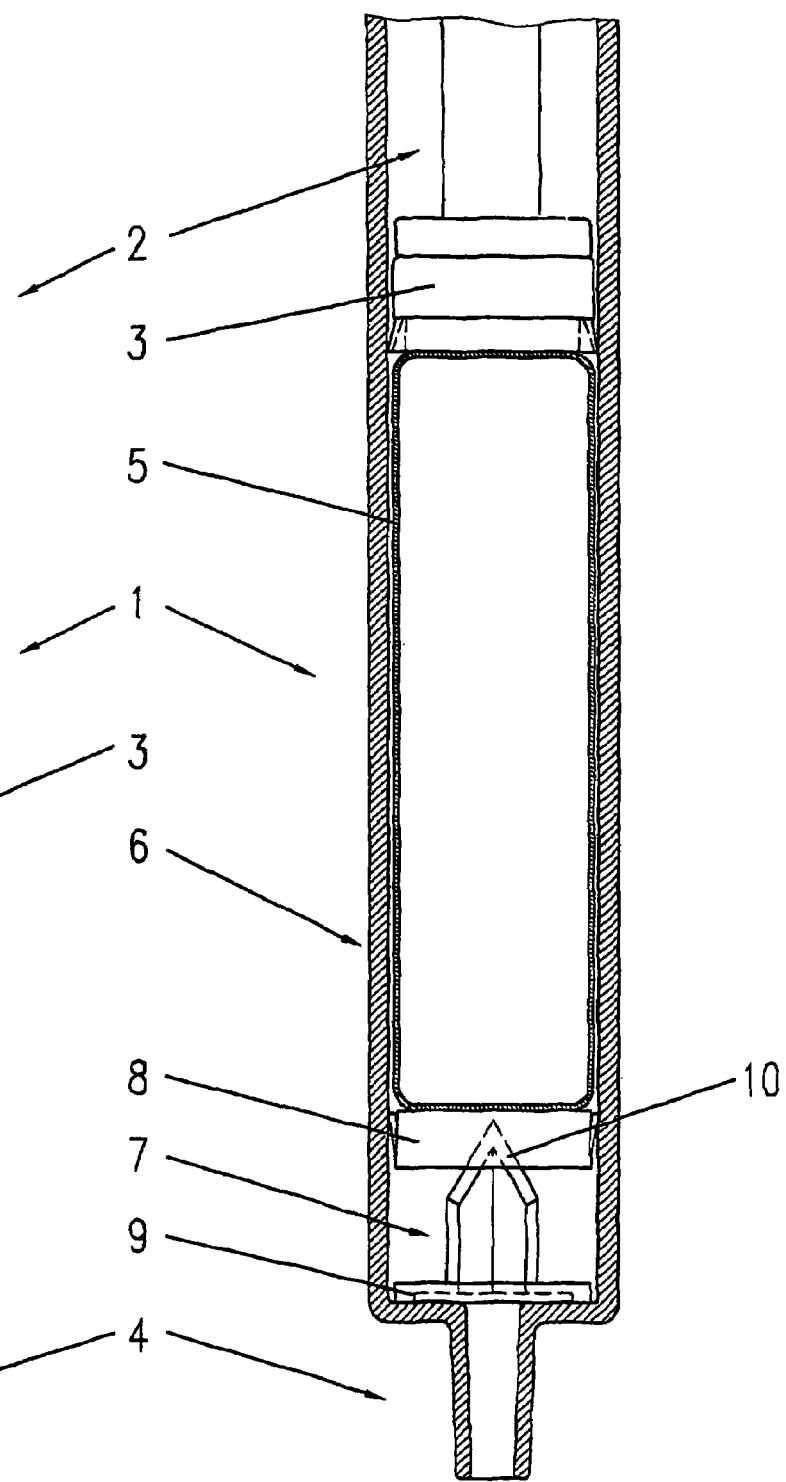
FIG. 2 shows a section according to line II-II with the device in a first position and FIG. 3 shows the device of FIG. 2 in a second position.

FIG. 1 illustrates a dispensing assembly in the form of a syringe 1 including a plunger 2, a piston 3 and an outlet 4 as well as a film bag 5 that is enclosed in container 6 of the syringe. A first exemplary embodiment of a bag piercing device 7 according to the invention is disposed at the outlet end of the container.

Figure 4:
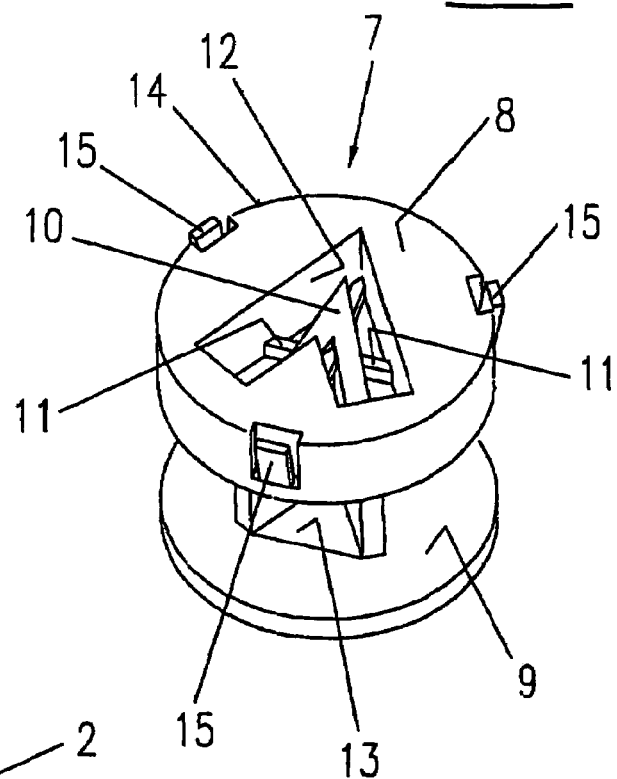
FIG. 4 shows a perspective view of the device of FIG. 2.

In FIG. 4, the device of the invention is shown in a perspective view, the device essentially comprising a bag support plate 8, a baseplate 9, and a piercing spike 10 that is connected to baseplate 9. The front side of the piercing spike forms a sharp-edged point.

Bag support plate 8 is connected to piercing spike 10 by collapsible or tearable pacers 11. In the present example, the piercing spike has a V-shaped horizontal projection as shown in FIG. 7A. The baseplate lies on the bottom at the outlet end of the container.

The dimensions of the collapsible or tearable spacers and their number are chosen in function of the selected material in such a manner that the collapsible or tearable spacers can withstand a certain pressure as it is e.g. created when the syringe is dropped or by shocks during its transport but that the collapsible or tearable spacers are broken, torn off or collapsed by the plunger respectively the piston at the beginning of the dispensing operation such that the baseplate is moved toward the outlet, thereby exposing the point of the piercing spike.

Figure 3:
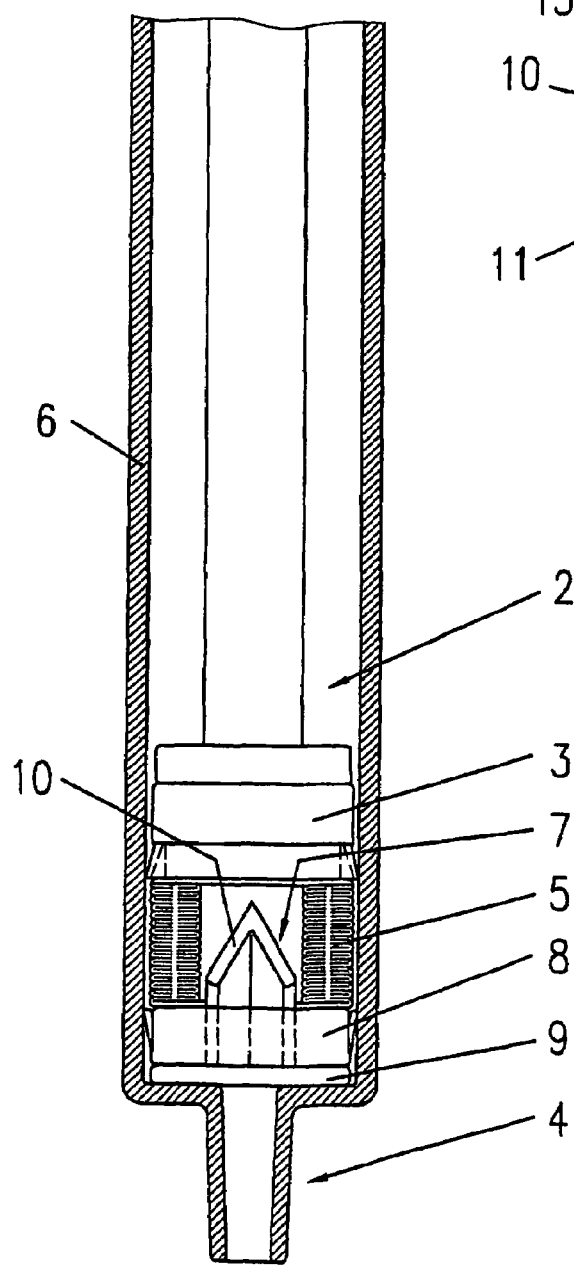

In FIG. 3 it is shown that after collapsible or tearable spacers 11 have been collapsed, torn off, or broken off, bag support plate 8 contacts the baseplate, thereby exposing the piercing spike. Film bag 5 is shown in the end position of the dispensing operation.

As follows from FIGS. 4 and 6, collapsible or tearable spacers 11 are attached to piercing spike 10, on one hand, and to opening 12 in the bag support plate 8, on the other hand. Opening 12 may have a cross-section that is similar to that of the piercing spike but larger in order to allow an unrestricted outflow of the dispensed substance from the bag. Baseplate 9 has an outflow opening 13 whose shape may also correspond to that of the piercing spike, as well as a recess 13A that is directed toward the bottom of the container and ensures that the liquid can reach the outlet.

In FIGS. 4 to 6 it is apparent that the bag piercing device 7 is designed as a unit that may preferably be injection-molded integrally from plastics. In this way it is possible to provide such piercing devices for the most diverse containers of dispensing assemblies or of syringes, including double or multiple syringes. To allow a better compensation of tolerances and to ensure a good centering effect, three elastic tongues 15 are arranged on external surface 14 of bag support plate 8, or other centering means may be provided.

In FIGS. 7B to 7D, different other cross-sections of piercing spikes are shown, for example a cruciform spike 16, see FIG. 7B, a circle arc-shaped spike 17, see FIG. 7C, and a straight, axially inclined spike 18, see FIG. 7D. Beyond that, other shapes are conceivable. Both the opening in bag support plate 8 and the outflow opening in baseplate 9 may be adapted to the particular shape of the spike.

The collapsible, respectively deformable and/or tearable spacers may take the most diverse shapes and are not limited to the exemplary embodiment.

In FIGS. 8 and 9, an embodiment having a doubly acting piercing device 19 is shown. Baseplate 20 is disposed between two piercing spikes 10 that are each provided with a respective bag support plate 8, these parts being identical to those of the preceding example. Collapsible or tearable spacers 11 are so designed that they are deformed or torn off in a determined order and thus open the package, e.g. a bag or a thin-walled container, in a defined manner. Instead of two bags 21 and 22 in one container 6, the container may alternatively have a partition wall in the forward portion or contain a thin-walled container in order to store a second material in the forward portion of the container.

Thus, for example, a bag containing a liquid may be enclosed in the rearward portion and a second bag or a container containing a powder or a gel in the forward portion. By opening and guiding the liquid in a defined manner, the liquid content of one bag can be transferred into another, previously closed bag or container or into a forward chamber separated by the partition wall.

As follows from the description, the term dispensing assembly is meant to include syringes or cartridges, double syringes or cartridges as well as pneumatically or electrically operated dispensing assemblies whose containers are designed to receive film bags or thin-walled containers.

The invention claimed is:

1. A device for piercing film bags, comprising:
   a piercing spike having a sharp edged point;
   a baseplate having the piercing spike on at least one of its sides;
   a bag support plate arranged over the baseplate such that the surface of the bag support plate facing the film bag is located above at a distance away from the point of the piercing spike; and
   spacers connecting the piercing spike to the bag support plate, the spacers being capable to be collapsed or torn off, the spacers being in the form of bridges that are attached to the piercing spike, on the one hand, and to the bag support plate, on the other hand;
   wherein the device is integrally formed of plastics.

2. A device according to claim 1, wherein the device is designed as a unit that is insertable into a container of a dispensing assembly.

3. A device according to claim 1, wherein the bag support plate has an annular surface, wherein a centering means being arranged on said annular surface.

4. A device according to claim 3, wherein the centering means include elastic tongues arranged on an external surface of the bag support plate.

5. A device according to claim 1, wherein the piercing spike has a V-shaped, cruciform, circular arc-shaped, or straight horizontal cross section in a plane that is perpendicular to a longitudinal direction in which the piercing spike extends, and its front portion is in the form of a sharp-edged point.

6. A device according to claim 1, wherein the device is a doubly acting device which has respective piercing spikes and bag support plates connected thereto by the collapsible or tearable spacers on both sides of a baseplate.

7. A device according to claim 1, wherein the bag support plate is arranged to contact a portion of the baseplate facing the bag support plate after the spacers have been collapsed or torn off.

8. A device according to claim 1, wherein the bag support plate defines a plane perpendicular to the piercing spike, and wherein the spacers are arranged substantially in said plane.

9. A device according to claim 1, wherein the bag support plate has an opening with a cross-section having the same shape as a cross-section of the piercing spike but a larger size than the cross-section of the piercing spike.

10. A device according to claim 9, wherein the spacers are attached to the bag support plate within the opening.

11. A device according to claim 1, wherein the baseplate has an outflow opening whose shape corresponds to the shape of the piercing spike.

12. A device according to claim 1, wherein the piercing spike does not protrude beyond the baseplate in a direction facing away from the bag support plate.

13. A device according to claim 1, wherein the baseplate is substantially flat.

14. A device for piercing film bags comprising:
a piercing spike having a point;
a baseplate having the piercing spike on at least one of its sides;
a bag support plate arranged over the baseplate such that the surface of the bag support plate facing the film bag is located at a distance from the point of the piercing spike; and
spacers connecting the piercing spike to the bag support plate, the spacers being capable to be collapsed or torn off, the collapsible or tearable spacers being in the form of bridges that are attached at a first portion to the piercing spike, and to the bag support plate at a second portion;
wherein the bag support plate is arranged to contact a portion of the baseplate facing the bag support plate after the spacers have been collapsed or torn off.

15. A device according to claim 14, wherein the bag support plate defines a plane perpendicular to the piercing spike, and wherein the spacers are arranged substantially in said plane.

16. A device according to claim 14, wherein the baseplate is substantially flat.

17. A device for piercing film bags comprising:
a piercing spike having a point;
a baseplate having the piercing spike on at least one of its sides;
a bag support plate arranged over the baseplate such that the surface of the bag support plate facing the film bag is located at a distance from the point of the piercing spike; and
spacers connecting the piercing spike to the bag support plate, the spacers being capable to be collapsed or torn off, the collapsible or tearable spacers being in the form of bridges that are attached to the piercing spike at a first portion, and to the bag support plate at a second portion;
wherein the bag support plate defines a plane perpendicular to the piercing spike, and wherein the spacers are arranged substantially in said plane.

\* \* \* \* \*